United States Patent [19]

Lau et al.

[11] Patent Number: 5,055,407

[45] Date of Patent: Oct. 8, 1991

[54] COMPOSITION AND METHOD OF ASSAYING AQUEOUS LIQUIDS FOR SPECIFIC GRAVITY

[75] Inventors: Arthur L. Y. Lau, Granger; James H. Pendergrass, South Bend, both of Ind.

[73] Assignee: Miles, Inc., Elkhart, Ind.

[21] Appl. No.: 215,358

[22] Filed: Jul. 5, 1988

[51] Int. Cl.$^5$ ............................................. G01N 33/52
[52] U.S. Cl. ......................................... 436/2; 422/57; 436/169
[58] Field of Search .................................. 422/56–57; 436/2, 169

[56] References Cited

U.S. PATENT DOCUMENTS

| | | | |
|---|---|---|---|
| 3,485,587 | 12/1969 | Keston | 422/56 |
| 4,015,462 | 4/1977 | Greyson et al. | 422/56 |
| 4,076,502 | 2/1978 | Dugle et al. | 422/56 |
| 4,318,709 | 3/1982 | Falb et al. | 422/57 |
| 4,376,827 | 3/1983 | Stiso et al | 422/56 |
| 4,473,650 | 9/1984 | Wang | 422/56 |
| 4,532,216 | 7/1985 | Wang | 422/56 |

FOREIGN PATENT DOCUMENTS 61-155757 7/1986 Japan .
62-006170 1/1987 Japan .

OTHER PUBLICATIONS

Fujita et al., "Color Reaction Between Pyrogallol Red–Molybdenum (IV) Complex and Protein", Bunsekikagaku vol. 32, pp E379–E387, 1983.

Watanabe et al., "Urinary Protein as Measured with a Pyrogallol Red–Molybdate Complex, Manually and in a Hatachi 726 Automated Analyzer", Clin. Chem. 32/8, pp. 1551–1554 (1986).

Primary Examiner—Robert J. Warden
Assistant Examiner—Lyle A. Alexander
Attorney, Agent, or Firm—Roger N. Coe

[57] ABSTRACT

A new and improved composition and method of determining the specific gravity of an aqueous test sample. The method includes using a test device comprising a carrier matrix incorporating a reagent composition capable of interacting with an aqueous test sample to produce a visually or instrumentally detectable and measurable response that correlates to the specific gravity of the aqueous test sample. The new and improved reagent composition, comprising a molybdate-dye complex indicator, such as a molybdatepyrocatechol violet complex; a protein, such as albumin; a chelating agent, like tartaric acid; and, if necessary, a suitable buffer, is incorporated into a carrier matrix, like filter paper, to provide increased sensitivity to test sample specific gravity and improved color differentiation between test samples having different specific gravities, thereby affording a more accurate and trustworthy specific gravity assay of an aqueous test sample, such as urine.

32 Claims, No Drawings

COMPOSITION AND METHOD OF ASSAYING AQUEOUS LIQUIDS FOR SPECIFIC GRAVITY

FIELD OF THE INVENTION

The present invention relates to a composition and a method of assaying for the specific gravity of an aqueous test sample. More particularly, the present invention relates to a new and improved method and composition for assaying an aqueous liquid, such as urine, for specific gravity by utilizing a test device comprising a reagent composition incorporated into a carrier matrix, such that a detectable and measurable response occurs upon contact of the test sample with the reagent composition. The response resulting from contact between the test sample and reagent composition can be correlated to the specific gravity of the test sample. The reagent composition provides increased sensitivity to test sample specific gravity and provides improved color differentiation between test samples of different specific gravity in order to more accurately measure, either visually or by instrument, the specific gravity of an aqueous test sample. In addition, the present invention relates to using a specific gravity reagent composition incorporated into a carrier matrix in an improved method to determine the specific gravity of an aqueous test sample by a dry phase, test strip assay procedure.

BACKGROUND OF THE INVENTION AND PRIOR ART

The specific gravity of an aqueous test sample, such as urine or serum, is a measure of the relative proportions of solid materials dissolved in the test sample to the total volume of the test sample. In general, the specific gravity of an aqueous test sample is a measure of the relative degree of concentration or the relative degree of dilution of the test sample. In regard to urine samples, the assay for specific gravity is important to help interpret the results of the other assays performed in a routine urinalysis. Clinically, under appropriate and standardized conditions of fluid restriction or increased fluid intake, the specific gravity of a urine sample measures the concentrating and diluting abilities of the kidneys of an individual.

Normally, the specific gravity of urine ranges from about 1.005 to about 1.030, but most often urine specific gravity ranges from about 1.010 to about 1.025. The specific gravity of urine is highest in the first morning urine specimen and generally is greater than 1.020. A specific gravity of about 1.025 or above in a random first morning urine specimen indicates a normal concentrating ability of the kidneys. The ability of the kidneys to concentrate urine can be measured by a concentration test. The concentration test is performed by withholding all fluids from the individual after the evening meal. Then the urine excreted during the night is discarded, and the first morning specimen is assayed. Clinically, a urine specific gravity of 1.025 or higher is considered normal, and indicates a normally functioning kidney.

Dilution tests also are used to determine the ability of the kidneys to concentrate liquids. However, these tests are less useful than the concentration tests because dilution tests provide less information about renal functions. Furthermore, dilution tests are potentially hazardous to the patient. For example, patients afflicted with certain diseases, such as Addison's disease, are advised to avoid dilution tests. The dilution test requires the patient to drink a suitable water load, usually about one liter during a 30-minute period. Then, within approximately one hour, normal patients will excrete at least one urine specimen with a specific gravity less than 1.003.

Either an abnormally low urine specific gravity or an abnormally high urine specific gravity is clinically significant. For example, diabetes insipidus, a disease caused by the absence of, or impairment to, the normal functioning of the antidiuretic hormone (ADH), is the most severe example of impaired kidney concentrating ability. This disease is characterized by excreting large urine volumes of low specific gravity. The urine specific gravity of individuals suffering diabetes insipidus usually ranges between 1.001 and 1.003. Low urine specific gravity also occurs in persons suffering from glomerulonephritis, pyelonephritis, and various other renal anomalies. In these cases, the kidney has lost its ability to concentrate the urine because of tubular damage.

An abnormally high urine specific gravity also is indicative of a diseased state. For example, the urine specific gravity is high in persons suffering from diabetes mellitus, adrenal insufficiency, hepatic disease, or congestive cardiac failure. The specific gravity likewise is elevated whenever there has been excessive loss of water, such as with sweating, fever, vomiting, and diarrhea. In addition, abnormally high amounts of certain urinary constitutents, in particular glucose and protein, increase the urine specific gravity of some individuals suffering from diabetes mellitus or nephrosis up to 1.050 or greater. As a general rule, the specific gravity increases 0.004 for every 1% glucose in urine and 0.003 for every 1% protein in urine. Furthermore, urine with a fixed low specific gravity of approximately 1.010 that varies little from specimen to specimen is known as isothenuric. This condition is indicative of severe renal damage with disturbance of both the concentrating and diluting abilities of the kidney.

Therefore, in order to determine if an individual consistently has either an abnormally high or an abnormally low urine specific gravity, and in order to help monitor the course of a medical treatment to determine its effectiveness, simple, accurate and inexpensive specific gravity assays have been developed. In general, the specific gravity of a test sample is a measurement that relates to the density of the test sample. The specific gravity is a value derived from the ratio of the weight of a given volume of a test sample, such as urine, to the weight of the same volume of water under standardized conditions (Eq. 1).

$$\text{Sp. Gr.} = \frac{\text{weight of urine}}{\text{weight of water}} \qquad \text{(Eq. 1)}$$

Water has a specific gravity of 1.000. Since urine is a solution of minerals, salts, and organic compounds in water, the specific gravity of urine is greater than 1.000. The relative difference reflects the degree of concentration of the urine specimen and is a measure of the total solids in urine.

Several methods are available to determine the specific gravity of urine. The most widely used method, and possibly the least accurate, employs a urinometer. The urinometer is a weighted, bulb-shaped instrument having a cylindrical stem containing a scale calibrated in specific gravity readings. The urinometer is floated in a cylinder containing the urine sample, and the specific gravity of the urine is determined by the depth the urinometer sinks in the urine sample. The specific gravity value is read directly from the urinometer scale at the junction of the urine with the air. The urinometer method is cumbersome and suffers from the disadvantages of requiring large volumes of urine test sample, difficult and inaccurate reading of the urinometer scale and unreliable assays because the urinometer is not regularly recalibrated. In addition, each urinometer is calibrated to read 1.000 in distilled water at a specific temperature indicated on each instrument. There is a change in the specific gravity of 0.001 for each 3° C. above and below this temperature. Therefore, for precise work, temperature corrections must be made on the readings Corrections also are recommended when glucose or protein is present in the urine sample.

Refractometry provides an indirect method of measuring the specific gravity of urine. The refractive index is the ratio of the velocity of light in air to the velocity of light in solution. The refractive index is not identical to the specific gravity of urine, but the refractive index can be correlated to the specific gravity. The refractive index of urine varies directly with the number of dissolved particles in urine and, therefore, varies directly with the specific gravity of urine. Consequently, measurement of the refractive index of urine can be related to the specific gravity of urine.

The refractometer method of determining the specific gravity of urine is desirable because specific gravity measurements are possible on as little as one drop of urine. The refractometer used to determine the refractive index is a small hand held instrument calibrated in terms of specific gravity, refractive index and total solid content. The refractometer requires a drop of urine placed in the appropriate sample slot in the refractometer. The instrument is held towards a light source and the assay, either in terms of specific gravity, refractive index, or solid content, is read directly from the calibrated scale located in the eyepiece. The specific gravity scale on the refractometer reads from 1.000 to 1.035 in increments of 0.001. The refractometer has the disadvantage of requiring daily calibration and not being amenable to home assays.

A third urinalysis method for specific gravity, the falling drop method, like the urinometer, is a direct measurement of urine specific gravity. In accordance with this method, a drop of urine is introduced into each of a series of columns that are filled with solvent mixtures of increasing and known specific gravity. When the drop of urine comes to rest after its initial momentum has dissipated and then neither rises nor falls, the specific gravity of the urine is determined to be the same as the solvent mixture of that particular column. In this procedure, a series of mixtures of xylene and bromobenzene, chloroform and benzene, or bromobenzene and kerosene have been employed. Prior to development of the refractometer, this technique had the advantage of requiring only a few drops of test sample to conduct a specific gravity assay. The falling drop method, however, never achieved widespread use in routine urinalysis because of the obvious time requirements in setting up such a system and the inability for an individual to perform the assay at home.

The falling drop method described above also can be performed instrumentally. Unlike the graded series of solvent mixtures described above, the instrument-based assay uses a specially designed column filled with a silicone oil having a controlled specific gravity and viscosity. The column is designed to measure the time required for a precisely measured drop of test sample to fall a distance defined by two optical gates (lamp-phototransistor pairs) mounted one above the other in a temperature-controlled column filled with a water-immiscible silicone oil of a slightly lower density than the test sample. The light beams from the lamps travel through the column oil and strike phototransistors located on the opposite wall of the column. A drop of urine dispensed into the column oil by a pipette breaks the beams of light as it falls through the oil. The urine drop breaking the upper beam starts an electronic timer, and breaking the lower beam stops the timer. The falling time is measured electronically and computed into specific gravity units. This specific gravity method is very precise, however, the cost of the assay instrument and the degree of skill required to operate the instrument makes home testing for urine specific gravity impractical.

Each of the above described instrument-based specific gravity assay methods has disadvantages, whereby none of the assay methods are particularly well suited to performing specific gravity assays outside of the physician's office or laboratory. Consequently, reagent impregnated test strips have been developed to allow specific gravity assays to be performed at home. The test strip assay developed for specific gravity measurements is an indirect assay method, wherein the test strip changes color in response to the ionic strength of the urine sample.

The present day specific gravity test strips comprise a carrier matrix impregnated with a reagent composition including three essential ingredients: a polyelectrolyte, such as a partially neutralized poly(methyl vinyl ether/maleic acid); a chromogenic indicator, such as bromothymol blue; and suitable buffering agents. This reagent composition is sensitive to the number of ions, or electrolytes, in the urine sample, such that the polyelectrolyte of the reagent composition undergoes a pKa (acid dissociation constant) change in relation to the ionic strength of the urine sample. Therefore, as the concentration of electrolytes in the urine increases (high specific gravity), the pKa of the polyelectrolyte present in the reagent composition decreases because free carboxyl groups are converted to carboxylate groups. The overall result is a pH decrease and a color transition of the bromothymol blue chromogenic indicator from blue-green to green to yellow-green in response to increased specific gravities. The resulting color transition, indicating a pH change caused by increasing ionic strength, or increasing specific gravity, is empirically related to the specific gravity of the test sample.

Some test strips used in specific gravity assays have a single test area consisting of a small square pad of a carrier matrix impregnated with the buffered polyelectrolyte and chromogenic indicator dye composition. Other test strips are multideterminant reagent strips that include one test area for the specific gravity assay as described above, and further include several additional test areas on the same strip to permit the simultaneous assay of other urinary constituents. For both types of reagent impregnated test strips, the assay for the specific gravity of urine is performed simply by dipping the test strip into a well mixed, uncentrifuged urine sample, then comparing the resulting color of the test area of the test strip to a standardized color chart provided on the test strip bottle For test strips utilizing the partially neutralized poly(methyl vinyl ether/maleic acid) polyelectrolyte and bromothymol blue indicator, semiquantitative assays for the specific gravity of aqueous test samples can be performed and reported as specific gravities ranging from 1.000 to 1.030. A reading of 1.000, or a blue-green color, indicates that the urine has a very low specific gravity, as demonstrated by the lack of a color transition of the chromogenic indicator dye. A specific gravity reading of from 1.005 to 1.030 is signified by color transitions, of from blue-green through green to yellow-green, that serve as reliable indicators of increasing specific gravity.

In accordance with the present day reagent strip method, an individual can readily determine, visually, that the specific gravity of a urine sample is in the range of about 1.000 to about 1.030. However, the sensitivity and the color resolution afforded by the presently available commercial test strips is insufficient to permit differentiation between liquid test samples having different, but nearly identical, specific gravities, such as specific gravities that differ by 0.003. The inability to differentiate between test samples having different, but nearly identical, specific gravities is important clinically because a healthy person usually has a urine specific gravity in the range of about 1.005 to about 1.030. Therefore, it could be important to more precisely determine a urine specific gravity that is either slightly above or slightly below these normal values, such that the accurate specific gravity assay can be interpreted in conjunction with assays for other urine analytes to provide a reliable diagnosis and to allow correct medical treatment to be instituted.

Therefore, it would be extremely advantageous to have a simple, accurate and trustworthy method of assaying for urine specific gravity that allows visual differentiation of specific gravity values within the ranges of 1.000 to about 1.005, about 1.005 to about 1.010, and about 1.010 to about 1.015, and upwards to between about 1.045 to about 1.050. By providing an accurate method of determining urine specific gravity in an easy to use form, such as a dip-and-read test strip, the urine assay can be performed by laboratory personnel to afford immediate test results. The specific gravity assay results can be interpreted in conjunction with assays for other urine constituents, such that a diagnosis can be made without having to wait for assay results and medical treatment can be commenced immediately. Furthermore, the test strip method can be performed by the patient at home to more precisely determine the specific gravity of the urine and therefore to help monitor the success of the medical treatment the patient is undergoing.

As will be described more fully hereinafter, the method of the present invention allows the fast, accurate and trustworthy assay for the specific gravity of urine by utilizing a test strip that includes a specific gravity reagent composition incorporating a molybdate-dye complex. The specific gravity reagent composition including the molybdate-dye complex improves the sensitivity of the assay and provides sufficient visual color differentiation between urine samples having specific gravities differing by as little as 0.003 in the specific gravity range of approximately 1.000 to approximately 1.030, and between urine samples having specific gravities differing by as little as 0.005 from approximately 1.030 to approximately 1.050. Therefore urine specific gravities of from approximately 1.000 to approximately 1.050 can be accurately determined.

The urine specific gravity of an individual depends upon the precise nature of his pathological disorder and upon the severity of his specific disease. An abnormally high or abnormally low urine specific gravity can be intermittent or continuous. Therefore, accurate and reliable specific gravity assays of urine and other aqueous test samples must be available for both laboratory and home use. The assays must permit the accurate measurement of abnormally low and abnormally high specific gravities, such that a correct diagnosis can be made and correct medical treatment implemented, monitored and maintained. In addition, it would be advantageous if the specific gravity assay method could be utilized in a dip-and-read format for the easy and economical determination of urine or other aqueous test sample specific gravities.

Furthermore, any method of assaying for the specific gravity of urine or other aqueous test samples must yield accurate, trustworthy and reproducible results by utilizing a specific gravity reagent composition that undergoes a color transition as a result of an interaction in response to the specific gravity of the test sample, and not as a result of a competing chemical or physical interaction, such as a pH change or preferential interaction with another test sample component, like protein or glucose. Moreover, it would be advantageous if the specific gravity assay method utilizing dry reagent strips provides for the rapid, economical and accurate determination of urine or other aqueous test sample specific gravities. Additionally, the method and composition utilized in the specific gravity assay should not adversely affect or interfere with the other test reagent pads that are present on multiple test pad strips.

Prior to the present invention, no known method of assaying urine or other aqueous test samples for specific gravity included a reagent composition providing sufficient sensitivity and color differentiation to allow accurate and trustworthy specific gravity assays to be made in the range of from about 1.000 to about 1.050. In addition, although a dry phase reagent test strip utilizing a partially neutralized polyelectrolyte and a dye, such as bromothymol blue, has been used extensively, no dry phase test strip has incorporated a molybdate-dye complex to provide sufficient sensitivity and sufficient visual color resolution to allow specific gravity differentiation between test samples having specific gravities differing by as little as 0.003.

The prior art contains numerous references to the polyelectrolyte-dye chemistry utilized in the specific gravity assay of urine. For example, U.S. Pat. Nos. 4,318,709 and 4,376,827 disclose the basic polyelectrolyte-dye technique used to assay for urine specific gravity. Both patents teach utilizing polyelectrolyte-dye chemistry to determine the specific gravity of urine by monitoring the color transition of the dye.

However, as will be fully described in the detailed description of the invention, the present invention provides a composition and method for the accurate determination of urine and other aqueous test sample specific gravities by utilizing a molybdate-dye complex as the indicator component of a specific gravity reagent composition. The molybdate-dye complex is known to interact with proteins in a test sample to produce a color transition. However, in accordance with an important feature of the present invention, it has been found that the color transition resulting from the interaction between the molybdate-dye complex and proteins is very sensitive to the ionic strength of the test sample, and therefore also is sensitive to the specific gravity of the test sample. As a result, it has been demonstrated that the sensitivity of the molybdate-dye complex and protein interaction to test sample ionic strength, or specific gravity, provides an indirect, but accurate, method of determining aqueous test sample specific gravities.

The publication "Color Reaction Between Pyrogallol Red-Molybdenum (VI) Complex and Protein", Y. Fujita, I. Mori, and S. Kitano, *Bunseki Kagaku*, 32, pp. E379–E386 (1983), first described the interaction between a protein and a pyrogallol red-molybdenum complex. The reported method required the incorporation of a chelating agent or metal ion into the molybdate-dye complex in order to determine the protein concentration of a test sample.

Similarly, Japanese Patent No. 61/155757 (1986) disclosed a colorimetric method of assaying for proteins in a test sample by using a composition including a molybdenum-dye complex and either a chelating agent or certain metal ions. However, it has been found that the method disclosed in Japanese Patent No. 61/155757 suffers from a severe ionic strength, or specific gravity, interference. It has been demonstrated that the degree of molybdate-dye complex binding to the protein, and therefore the degree of color transition, is inversely related to the ionic strength of the sample. As a result, the assay of a urine sample of low ionic strength (low specific gravity) produces a greater color transition in the test device (therefore indicating a greater protein content) than the assay of a urine sample having the same protein content, but a higher ionic strength (higher specific gravity). Unexpectedly, the specific gravity reagent composition utilized in the present invention takes advantage of the ionic strength/specific gravity interference found in the protein assays to provide accurate specific gravity assays regardless of other test sample components, such as proteins The publication, "Urinary Protein as Measured with a Pyrogallol Red-Molybdate Complex, Manually and in a Hitachi 726 Automated Analyzer", N. Watanabe, S. Kamei, A. Ohkubo, M. Yamanaka, S. Ohsawa, K. Makino and K. Tokuda, *Clin. Chem.*, 32/8, pages 1551–1554 (1986), further describes the method disclosed in Japanese Patent No. 61/155757. The Watanabe publication describes the automated or manual detection of proteins in urine using a molybdate-dye complex. The publication reports that the interaction of interest between the protein and the molybdate-dye complex continued for at least eight minutes and is complete within 10 minutes at 37° C. for automated assays, but for manual assays, the interaction was allowed to continue for 20 minutes before the assay was examined for a response. In addition, to the ionic strength interference described above, such a long interaction time for the complete color transition to occur is both inconvenient and can lead to erroneous assays should the degree of color transition, and hence protein content, be determined too quickly. However, according to the method of the present invention, the assay for the specific gravity of a test sample using a specific gravity reagent composition including a molybdate-dye complex is essentially complete in less than two minutes, therefore providing fast specific gravity results with a greatly reduced probability of an erroneous assay.

In contrast to the prior art, and in contrast to the presently available commercial test strips, the method of the present invention provides increased sensitivity in the measurement of urine specific gravity by utilizing a specific gravity reagent composition including a molybdate-dye complex, thereby achieving an accurate specific gravity assay, such as to within 0.003 for liquids having a specific gravity of from about 1.000 to about 1.030, and to within 0.005 for liquids having a specific gravity of from about 1.030 to about 1.050. Unexpectedly and surprisingly, the method of the present invention, also in contrast to the prior art, allows the simple and fast measurement of the specific gravity of a liquid test sample. Hence, in accordance with the method of the present invention, new and unexpected results are achieved in the dry phase reagent strip assay of urine and other aqueous test samples for specific gravity, in the range of from about 1.000 to about 1.050, by utilizing a specific gravity reagent composition including a molybdate-dye complex.

SUMMARY OF THE INVENTION

In brief, the present invention is directed to a new and improved method and composition for determining the specific gravity of a liquid test sample, especially the specific gravity of aqueous test samples such as urine and serum. The method includes using a reagent composition capable of interacting with a test sample to produce a detectable and measurable response that can be correlated to the specific gravity of the test sample. For home use, the reagent composition produces a visually detectable response. For laboratory use, the reagent composition produces a response that is detectable visually or by instrument. The method is suitable for dry phase assays, wherein the specific gravity reagent composition is incorporated into a carrier matrix of a detection device. The carrier matrix of the detection device comprises such bibulous porous materials as filter paper, or such nonbibulous porous materials as a permeable strip, layer or membrane of a polymeric material. A specific gravity reagent composition is homogeneously incorporated into the carrier matrix, and the carrier matrix then holds the specific gravity reagent composition homogeneously throughout the carrier matrix in a known concentration while maintaining carrier matrix penetrability for the liquid test sample.

More particularly, the present invention is directed to a method of assaying for the specific gravity of urine or other aqueous test samples by utilizing a new and improved specific gravity reagent composition. It has been demonstrated that employing a reagent composition including a molybdate-dye complex provides sufficiently increased sensitivity to test sample specific gravity and sufficient color differentiation between test samples of different specific gravity to permit the accurate measurement of the specific gravities of aqueous test samples. In accordance with an important feature of the present invention, the specific gravity of urine and other test samples can be accurately determined between about 1.000 and about 1.050, and especially between about 1.005 and about 1.035. By utilizing a molybdate-dye complex in the specific gravity reagent composition of the present invention, the specific gravity of urine or other aqueous test samples can be more accurately determined because the improved sensitivity of the method and the improved color differentiation between samples of different specific gravity is achieved by the specific gravity reagent composition. Furthermore, surprisingly and unexpectedly, the specific gravity reagent composition, including the molybdate-dye complex, incorporated into the specific gravity detection device allows the accurate measurement of specific gravities, such as between about 1.000 and about 1.050, and especially between about 1.005 and about 1.035, in urine and other test samples to within about 0.003 for urine and other test samples having a specific gravity of from about 1.000 to about 1.030, and to within about 0.005 for urine and other test samples having a specific gravity of from about 1.030 to about 1.050.

Therefore, it is an object of the present invention to provide a new and improved method and composition for determining the specific gravity of an aqueous liquid.

Another object of the present invention is to provide a simple, trustworthy, accurate and reproducible method of assaying urine or other aqueous test samples for specific gravity.

Another object of the present invention is to provide a new and improved composition for interaction with an aqueous test fluid to produce a visible change, such as a change in color of a test device, that is indicative of the specific gravity of the test fluid.

Another object of the present invention is to provide a method of assaying urine or other aqueous test samples that provides sufficient sensitivity and sufficient visual color resolution to allow the differentiation between and measurement of specific gravities.

Yet another object of the present invention is to provide a method of assaying urine or other aqueous test samples that is sensitive to specific gravities of between about 1.000 and about 1.050 and that differentiates between test samples having specific gravities differing by as little as about 0.003 for test samples having a specific gravity of from about 1.000 to about 1.030 and differing by as little as about 0 005 for test samples having a specific gravity of from about 1.030 to about 1.050.

Another object of the present invention is to provide a method of assaying urine or other aqueous test samples that utilizes an indicator reagent composition.

Another object of the present invention is to provide a method of assaying urine or other aqueous test samples by utilizing a specific gravity indicator reagent composition that can interact with components of the urine or other aqueous test sample and undergo a detectable and measurable color transition to establish the specific gravity of the test sample.

Another object of the present invention is to provide a specific gravity reagent composition that can interact with test sample components and undergo a visually and/or instrumentally differentiable color transition to allow the determination of the specific gravity of the urine or other aqueous test samples at levels of from about 1.000 and about 1.050, and especially from about 1.005 and about 1.035.

Another object of the present invention is to provide a method of assaying for the specific gravity of a liquid test sample by incorporating a specific gravity reagent composition including a molybdate-dye complex into a dry phase detection device.

Still another object of the present invention is to provide a new and improved method of assaying for the specific gravity of an aqueous test sample by utilizing a test device including a carrier matrix having incorporated therein a specific gravity reagent composition capable of interacting with the components of the test sample, wherein the carrier matrix comprises a bibulous matrix, like filter paper, or a nonbibulous matrix, like a layer, film or membrane of a permeable polymeric material.

A still further object of the present invention is to provide a new and improved dry phase test strip capable of incorporating a specific gravity reagent composition comprising a molybdate-dye complex into the carrier matrix to achieve a test strip of new and unexpected precision in response to the specific gravity of a liquid test sample.

The above and other objects and advantages and novel features of the present invention will become apparent from the following detailed description of the invention.

DETAILED DESCRIPTION OF THE INVENTION

In accordance with the method of the present invention, the specific gravity assay of urine and other aqueous test samples is accomplished by utilizing a specific gravity indicator reagent composition including a molybdate-dye complex. By employing a specific gravity reagent composition including a molybdate-dye complex, sufficient sensitivity and sufficient visual color differentiation between test samples of differing, specific gravities is achieved. Therefore, the accurate and reproducible specific gravity assay of aqueous test samples is possible. In addition, the improved sensitivity and color resolution to test sample specific gravities afforded by the method of the present invention is especially useful in urine assays.

Present-day commercial specific gravity assays are incapable of effectively differentiating between differing, but almost identical, specific gravities. However, in accordance with the method and composition of the present invention, specific gravities between about 1.000 and about 1.050, and especially between 1.005 and 1.035, can be differentiated from almost identical, specific gravities and accurately measured. Differentiating between specific gravity levels is clinically important because urine specific gravities that are either above or below the normal specific gravity range of from about 1.010 to about 1.025 for a healthy individual may indicate a potential renal deficiency. An accurate urine specific gravity assay interpreted in conjunction with assays for other urine analytes may assist in diagnosing a diseased state. It should be noted that in regard to urine specific gravities within the relatively normal range of from about 1.010 to about 1.025, the method of the present invention still affords improved color differentiation and improved sensitivity to urine specific gravity. However, clinical benefits are realized in this normal specific gravity range by interpretation of the specific gravity assay in conjunction with urine assays for other analytes, such that all of the assays can provide information concerning an abnormal physiological state that must be investigated further.

Furthermore, it will become apparent that in addition to assaying urine, the method and composition of the present invention also can be used to determine the specific gravity of blood plasma and serums; and more generally, the specific gravity of many other physiologic fluids as well. To achieve the full advantage of the present invention, the method and composition of the present invention is employed in dry phase, test pad assays to determine the specific gravity of urine or other aqueous test samples.

Surprisingly and unexpectedly, it has been found that a specific gravity reagent composition including a molybdate-dye complex demonstrated improved and increased sensitivity to test sample specific gravity and improved visual color differentiation between test samples of differing specific gravity when used in a dye-binding technique to determine the specific gravity of an aqueous test sample. The dyebinding technique using the molybdate-dye complex specific gravity reagent composition provides a more accurate and trustworthy specific gravity assay, such that a test sample specific gravity to within 0.003 can be determined.

The dyes presently used in specific gravity assays undergo different color transitions due to a pKa (acid dissociation constant) change in a polyelectrolyte, such as a partially neutralized poly(methyl vinyl ether/-maleic acid), upon contacting urine of different ionic strengths, or specific gravities. The phenomena is fully described in Falb et al U.S. Pat. No. 4,318,709, wherein the various dyes, the polyelectrolytes and the buffers required to observe the pKa change are disclosed. The Falb et al patent basically describes the present day dry phase test strips employed to assay for the specific gravity of urine. These test strips generally include an indicator dye that normally undergoes a color transition in the neutral pH range of about 6 to about 8, such as bromothymol blue; and a partially neutralized polyelectrolyte. The pKa of the partially neutralized polyelectrolyte decreases as the ionic strength of the urine increases. The overall result is a drop in pH, and the bromothymol blue indicator changes color from blue-green to green to yellow-green in response to the pH change caused by increasing ionic strength. The increase in ionic strength of an aqueous test sample is directly related to an increase in specific gravity; the color transition of the dye therefore is empirically related to specific gravity values. This present day method allows specific gravities to be determined to within about 0.005.

Japanese Patent No. 61/155757 (1986) describes the use of a molybdate-dye complex and either a chelating agent or a certain metal ion to assay for protein in liquid samples. However, as discussed above, the Japanese method suffers from a serious ionic strength/specific gravity interference such that liquid samples having the same protein content but different ionic strengths/-specific gravities will yield different protein assays. However, in accordance with an important feature of the present invention, it has been demonstrated that the ionic strength/specific gravity interference observed in protein assays can be used in a method to accurately assay for the specific gravity of urine and other aqueous test samples. Surprisingly and unexpectedly, using a molybdate-dye complex in a reagent composition to determine the specific gravity of a test sample provides a more accurate and trustworthy specific gravity assay of aqueous samples than the polyelectrolyte-dye method presently used in dry phase test strips. In addition to more reliable specific gravity assays, the method of the present invention provides rapid specific gravity assay results. Therefore, a method of accurate, reproducible and trustworthy specific gravity assays, performable at home or in the laboratory to yield essentially immediate specific gravity assay results, is achieved.

In order to achieve the benefits afforded by the method of the present invention, the specific gravity reagent composition must include a molybdate-dye complex as the indicator component of the composition. In contrast both to the prior art and to presently available commercial specific gravity assays, the incorporation of a molybdate-dye complex as the indicator component of the specific gravity reagent composition provides improved color resolution and differentiation, both visually and instrumentally, of the color transition occurring upon interaction of the indicator with the aqueous test sample. Therefore, the sensitivity of the specific gravity assay, especially to liquids having different, but almost identical, specific gravities, is increased.

The method of the present invention utilizes the effects of the ionic components of the aqueous test sample upon the color formed between a protein and a molybdate-dye complex. The incorporation of a molybdate-dye complex as the indicator component of a specific gravity reagent composition allows the specific gravity of test liquids to be accurately and reliably measured, such that specific gravity values can be measured to within 0.003 for aqueous test samples having a specific gravity of from about 1.000 to about 1.030 and to within 0.005 for aqueous test samples having a specific gravity of from about 1.030 to about 1.050. As previously described, when a polyelectrolyte interacts with the ionic components of a test sample, the apparent pKa of the polyelectrolyte is altered, the pH decreases, and a color transition in a pH indicator dye occurs. However, in accordance with an important feature of the present invention, the molybdate-dye complex of the specific gravity reagent composition similarly interacts with the ionic components of the test sample, but a more spectacular color transition is achieved. Therefore improved specific gravity assay sensitivity, and improved color resolution and differentiation between test samples of different specific gravity, occurs upon interaction of the specific gravity reagent composition with ionic test sample components, thereby achieving the more accurate measurement of test sample specific gravity.

In general, the indicator component of the specific gravity reagent composition utilized in the method of the present invention is a complex formed as a result of an interaction between a molybdate and a dye compound. It is of primary importance that the molybdate-dye complex is capable of interacting with the ionic components of the aqueous test sample and is capable of undergoing a detectable and measurable color transition in response to the molybdate-dye complex-ionic component interaction. The molybdatedye complex utilized in the specific gravity reagent composition must preferentially interact with ionic components of the test sample as opposed to any competing chemical or physical interactions with other components in the test sample. Any appreciable competing interactions could lead to false and erroneous assays concerning the specific gravity of the test sample. For example, the proper pH adjustment and buffering of the specific gravity reagent composition precludes the possibility of a color transition occurring because of a pH change in all cases except those wherein the test sample is sufficiently alkaline to overcome the effect of the buffers. In accordance with the method of the present invention, the pH of the molybdate-dye complex is adjusted to and is buffered at a pH value slightly below the pH range wherein the molybdate-dye complex changes color in order for the molybdate-dye complex to undergo its maximum color transition, and therefore most substantially increase specific gravity assay sensitivity and most appreciably improve color resolution. Therefore, samples having different, but almost identical, specific gravities, are more readily and accurately differentiated and assayed.

Furthermore, the dye employed in the molybdate-dye complex of the specific gravity reagent composition must undergo a sufficiently intense color transition such that the relatively low concentrations of ionic components normally present in a test sample of low specific gravity will produce a detectable and measurable color transition. For example, the benefits of improved color resolution and increased assay sensitivity can be defeated or minimized if the molybdatedye complex undergoes an insufficient color transition from a first color to a second color. Therefore, in order to achieve the full advantage of the present invention, the dyes employed in the molybdate-dye complex of the specific gravity reagent composition are selected such that the dye undergoes a sufficient color change either from a more intense color to a less intense color, or from a less intense color to a more intense color, to permit the assayer, either visually or by instrument, to detect a color transition and measure the specific gravity of the test sample.

It has been found that the dye of the molybdate-dye complex used most advantageously in the method of the present invention is a polyhydroxybenzenesulfonephthalein-type dye, having a structure similar to the dyes pyrocatechol violet and pyrogallol red, illustrated below in structural formulas I and II, respectively.

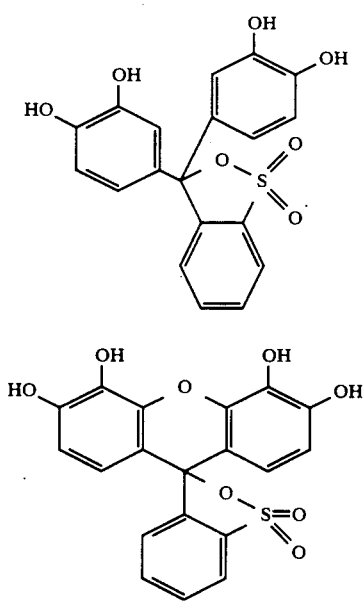

Suitable dyes having the polyhydroxy-substituted benzenes and a sulfonephthalein-type structure in addition to pyrocatechol violet and pyrogallol red include, but are not limited to, bromopyrogallol red, xylenol orange and pyrogallol phthalein; and mixtures thereof. Similarly, the polyhydroxybenzenephthalein-type indicators, such as pyrogallolphthalein, depicted in structural formula III, and o-hydroxyhydroquinonphthalein also can be used in the method and composition of the present invention.

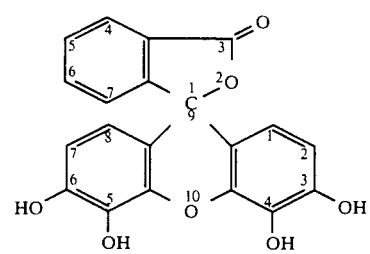

These polyhydroxybenzenesulfonephthalein-type dyes and polyhydroxybenzenephthaleintype dyes can complex to metal oxides, such as molybdates and phosphomolybdates; can interact with the ionic components of the test sample after complexing with a metal oxide; and can undergo a sufficient color transition after complexing and then interacting with ionic components of the test sample to allow the visual and/or instrumental measurement of the specific gravity of a test sample. Depending upon several chemical and physical parameters, such as ability to interact with the ionic components of the test sample, color of the test sample, intensity of the color transition and chemical compatibilities, a particular polyhydroxybenzenesulfonephthaleintype dye, or polyhydroxybenzenephthalein-type dye, is selected for complexing with the molybdate, or phosphomolybdate, to form the indicator component of the specific gravity reagent composition.

The exact polyhydroxybenzenesulfonephthalein-type dye, or polyhydroxybenzenephthalein-type dye, selected as the dye compound of the molybdate-dye complex component of the specific gravity reagent composition can be determined by those skilled in the art of designing test kits in order to produce a specific gravity assay having maximum visual color resolution and maximum sensitivity. The polyhydroxybenzenesulfonephthalein-type dyes and polyhydroxybenzenephthalein-type dyes utilized in the molybdatedye complex compound of the specific gravity reagent composition of the present invention can be prepared by methods well known to persons in the art. Furthermore, several dye compounds that are useful in the method of the present invention are well known indicator dyes that are presently available commercially.

In accordance with another important feature of the present invention, the polyhydroxybenzenesulfonephthalein-type dye or polyhydroxybenzenephthalein-type dye must be combined with a molybdate salt to form the molybdate-dye complex indicator component of the specific gravity reagent composition. The molybdate salt utilized in the molybdate-dye complex is not particularly limited. However, the molybdate salt must have sufficient water solubility such that the molybdate salt can be solubilized for complexing with the polyhydroxybenzenesulfonephthalein-type or polyhydroxybenzenephthalein-type dye. Furthermore, it is preferred that the molybdate salt utilized in the present invention is essentially colorless in order to avoid assay interferences due to a highly colored molybdate cation. Molybdate salts exhibiting sufficient water solubility to allow complexing with the polyhydroxybenzenesulfonephthalein-type or polyhydroxybenzenephthalein-type dyes include, but are not limited to, ammonium molybdate, sodium molybdate, bismuth molybdate, cadmium molybdate, calcium molybdate, lithium molybdate, magnesium molybdate, potassium molybdate, strontium molybdate, zinc molybdate, alkylammonium or hydroxyalkylammonium molybdates, dialkylammonium or di(hydroxyalkyl)ammonium molybdates, trialkylammonium or tri(hydroxyalkyl)ammonium molybdates and ammonium phosphomolybdates; or combinations thereof.

In accordance with an important feature of the present invention, the preferred molybdate salts used to complex with the polyhydroxybenzenesulfonephthalein-type or polyhydroxybenzenephthalein-type dye are the highly water-soluble molybdate salts and those molybdate salts including colorless, non-complexing and non-interfering metal and ammonium cations To achieve the full advantage of the present invention, ammonium molybdate, potassium molybdate, sodium molybdate, lithium molybdate, strontium molybdate, ammonium phosphomolybdate and the alkyl- or hydroxyalkylsubstituted ammonium molybdates, or combinations thereof, are used as the molybdate salt to form the molybdate-dye complex of the present invention.

In addition to the dye and the molybdate salt, the specific gravity reagent composition also must contain a sufficient amount of a protein. It has been shown that a molybdate-dye complex can bind to a protein and undergo a color transition. The color transition can be correlated to the protein content of a test sample. Furthermore, as will become apparent hereinafter, it has been shown that the protein determination using a molybdate-dye complex is dependent upon the ionic strength, or specific gravity, of the test sample. For example, as the ionic strength of the test sample increases, the binding that occurs between the protein and the molybdate-dye complex decreases, and therefore, the color transition is not as intense. As a result, a sample of low specific gravity gives a greater color transition than a sample having the same protein content but a higher specific gravity. Therefore, a relatively large amount of protein is incorporated into the specific gravity reagent composition of the present invention to insure sufficient binding between the molybdate-dye complex and the protein, and also to eliminate any interference that a relatively small amount of protein in the test sample might provide.

The specific gravity reagent composition of the present invention also must contain a chelating agent in order to provide sufficient color differentiation between test samples having different, but almost identical, specific gravities. It has been found that if the chelating agent is omitted, the color transition resulting from the interaction between the specific gravity reagent composition and the ionic components of the test sample cannot be sufficiently differentiated for test samples having specific gravities within 0.005 of each other. Therefore, in order to achieve the new and unexpected results of the present invention, a chelating agent, such as tartaric acid or oxalic acid, must be included in the specific gravity reagent composition.

The chelating agent utilized in the present invention is not particularly limited, however, usually an organic chelating agent, like a chelating dicarboxylic acid or a chelating polycarboxylic acid or like the polycarboxylated amino acid-type chelating agents, such as ethylenediaminetetraacetic acid, are most preferably employed. Suitable chelating agents for use in the specific gravity reagent composition of the present invention include, but are not limited to, tartaric acid, oxalic acid, malonic acid, succinic acid, citric acid, ethylenediaminetetraacetic acid (EDTA), gluconic acid, N-(hydroxyethyl)ethylenediaminetriacetic acid (HEEDTA), nitrilotriacetic acid (NTA), diethylenetriaminepentaacetic acid (DTPA), aminotris(methylene phosphonic acid), hydroxy-ethylidene diphosphonic acid, hexamethylenediaminetetra(methylene phosphonate), ethylenediaminediacetic acid (EDDA), iminodiacetic acid (IDA), nitrilopropionic acid (NTP), hydroxyethyliminodiacetic acid (HIDA), pyrophosphoric acid, 1-hydroxyethane-1,1-diphosphonic acid, tripolyphosphoric acid, hexametaphosphoric acid, and metaphosphoric acid; or combinations thereof. The chelating agent can be added to the specific gravity reagent composition in the free acid form, or in the form of a water-soluble salt, such as the sodium, potassium, lithium, ammonium, an alkyl-substituted ammonium or a hydroxyalkyl-substituted ammonium salt. The chelating agent is added to the specific gravity reagent composition in an amount ranging from about 0.1g to about 2.0g per 100 dL of the specific gravity reagent composition. Within this range, it has been found that the chelating agent is present in sufficient quantity to help provide sufficient color differentiation between test samples having different, but almost identical, specific gravities.

A complex of a polyhydroxybenzenesulfonephthalein-type or polyhydroxybenzenephthaleintype dye and a suitable molybdate salt is utilized as the indicator component of a specific gravity reagent composition that also includes a sufficient amount of a protein and a chelating agent in an improved method to determine the specific gravity of urine or other liquid test samples. It has been demonstrated that the specific gravity reagent composition of the present invention interacts with the ionic components, or electrolytes, of the test sample to produce a differentiable and measurable color transition, either visually and/or by instrument. However, in addition to the molybdate-dye complex, the chelating agent and the protein, the specific gravity reagent composition of the present invention also may require a sufficient amount of a proper buffer, such that the molybdate-dye complex will not change color as a result of a pH shift, but will change color upon contact and interaction with the ionic components of the test sample to accurately establish the specific gravity of the test sample.

Further, it has been demonstrated that any of various known types of buffers can be used in the specific gravity reagent composition of the present invention. The function of the buffer is to maintain the specific gravity reagent composition at a substantially constant pH to produce the desired color transition in the specific gravity reagent composition because of the presence of ionic components in the test sample and to essentially eliminate color transitions due to a variation in the pH of the test sample. As a result, the amount of buffer incorporated into the specific gravity reagent composition depends upon the nature of the test sample. The quantity of buffer usually falls between about 100 millimolar (mM) and about 500 millimolar, although in particular cases the amount of buffer can be above or below this range. The nature of the buffer used will depend upon, and vary with, the molybdate-dye complex incorporated into the specific gravity reagent composition. However, it has been found that for optimum results, the pH of the specific gravity reagent composition generally should be maintained at a pH value only slightly below the pH range wherein the molybdate-dye complex of the specific gravity reagent composition undergoes a color transition, normally in the pH range of approximately 2 to approximately 4, and preferably in the range of approximately 2 to approximately 3. A method of determining a suitable buffered pH value for the particular indicator dyes of the specific gravity composition and of determining the particular buffer that can be used in the specific gravity reagent composition is found in Keston, U.S. Pat. No. 3,485,587.

Although the use of a buffer in the present specific gravity reagent composition is preferred, a buffer is not essential in all cases. For example, in special cases it may be desirable to add a buffer to the urine or other test sample before the test sample contacts the specific gravity reagent composition. Also the test sample may already contain a buffer of the proper type and in the proper amount to maintain the specific gravity reagent composition at a constant pH, or the specific gravity reagent composition may be insensitive to pH changes. Furthermore, in some cases the chelating agent utilized in the specific gravity reagent composition also may serve as the buffer. In such cases, the molybdate-dye complex, the chelating agent and the protein can be the sole active ingredients in the specific gravity reagent composition. However, it should be understood that optional ingredients, such as surfactants, that do not materially alter the nature and the function of the molybdate-dye complex, the chelating agent, the protein and/or the buffer and that do not interfere with the specific gravity assay, also can be included in the specific gravity reagent composition. Likewise, other such non-essential ingredients include polymers, plasticizers and nonactive background dyes.

Upon contact with the urine or other aqueous test sample, the molybdate-dye complex of the specific gravity reagent composition undergoes a color transition and reveals the specific gravity of the test sample. The intensity and degree of the color transition can be used to determine the specific gravity of the test sample by comparing or correlating the color produced by the test sample to colors produced by solutions having a known specific gravity In accordance with an important feature of the present invention, it has been demonstrated that the specific gravity reagent composition provides a sufficiently resolved and differentiated color transition such that the specific gravity of the test sample can be measured and accurately determined to within about 0.003 for test samples having a specific gravity of from about 1.000 to about 1.030 and to within about 0.005 for test samples having a specific gravity of from about 1.030 to about 1.050 without the use of colormeasuring instruments, such as spectrophotometers or colorimeters. However, if desired, such colormeasuring instruments can be used to measure the difference in color degree and intensity between the test sample and a solution of known specific gravity.

Accordingly, the specific gravity assay method of the present invention, utilizing a suitably buffered specific gravity reagent composition including a molybdate-dye complex, a chelating agent and a protein, improves the accuracy and reliability of the specific gravity assay and also increases physician confidence in the specific gravity assay. Additionally, because of the number of urine assays for specific gravity being performed at home by the untrained patient, as opposed to trained physicians or technicians in the laboratory, it is imperative to provide accurate and reliable assay methods for the specific gravity of urine and serum.

In general, assays for specific gravity have been conducted at an essentially neutral pH and using an indicator dye undergoing a color transition at an essentially neutral pH in response to a pKa change and a pH decrease in a polyelectrolyte. In accordance with the method and composition of the present invention, an increased interaction between the molybdate-dye complex, the chelating agent and the protein of the specific gravity reagent composition occurs at low pH values because of a strong attraction between the positively-charged cationic protein molecule and the negatively-charged anionic indicator dye molecule, and, additionally, because the acidic conditions serve to partially denature proteins and therefore increase the ability of the protein to interact with the indicator dye. Therefore, the specific gravity reagent composition is adjusted to and maintained at an acidic pH. Generally, the pH of the system is adjusted to and maintained at between about 2.0 and about 4.0; and to achieve the full advantage of the present invention the pH is adjusted to and maintained at between about 2.0 and about 3.0.

To demonstrate the new and unexpected results achieved by the method and composition of the present invention, a specific gravity reagent composition, including a complex formed between ammonium molybdate and the polyhydroxybenzenesulfonephthalein-type dye, pyrocatechol violet, was prepared, then used in a dry phase assay for the specific gravity of a test sample. In addition to the molybdate-pyrocatechol violet complex, the specific gravity reagent composition includes albumin as the protein that binds to the molybdate-dye complex and masks the interfering effects of any protein present in the test sample and tartaric acid as the chelating agent. The specific gravity reagent composition is adjusted to, and maintained at, a pH of approximately 2.5. The aqueous solution of the molybdate-pyrocatechol violet complex, albumin and tartaric acid is dark blue in color and, after incorporation into a suitable carrier matrix changes color ranging from blue to yellow after contact and interaction with test samples having an increasing specific gravity. As a result, a specific gravity reagent composition including the appropriate amounts of a molybdate, like ammonium molybdate; a dye, like pyrocatechol violet; a chelating agent, like tartaric acid; and a protein, like albumin, adjusted to and maintained at a suitable pH with a suitable buffer, after incorporation into a suitable carrier matrix, produced the color transitions summarized in TABLE I upon contact and interaction with standard solutions having the following specific gravities: = MS-1538

TABLE I

COLOR TRANSITION OF AMMONIUM MOLYBDATE-PYROCATECHOL VIOLET COMPLEX SPECIFIC GRAVITY REAGENT COMPOSITION UPON INTERACTION WITH STANDARD SOLUTIONS (pH = 2.5)

| Specific Gravity of Standard Solution | Observed Color |
|---|---|
| 1.000 | Dark Blue |
| 1 005 | Blue |
| 1.010 | Blue-Green |
| 1.015 | Green |
| 1.020 | Light Green |
| 1.030 | Yellow-Brown |
| 1.050 | Yellow |

In accordance with an important feature of the present invention, the improved color resolution achieved by using the molybdate-pyrocatechol violet complex in the specific gravity reagent composition permits not only measurement, but also differentiation between specific gravities differing by as little as 0.003, such as specific gravities of 1.000, 1.003 and 1.005 over the specific gravity range of about 1.000 to about 1.030; and by as little as 0.005 over the specific gravity range of about 1.030 to about 1.050. In contrast, the prior art methods employing an indicator dye to determine specific gravity are unable to differentiate between specific gravities differing by less than about 0.005, and provide only minimal differentiation between specific gravities differing by only 0.005, because of insufficient color resolution. However, in accordance with the method and composition of the present invention, increased assay sensitivity is achieved, such as down to 0.003, to ultimately yield more accurate and meaningful assay results.

In accordance with the method of the present invention, to perform a dry phase, test strip assay for specific gravity, the specific gravity reagent composition is produced first. For example, a specific gravity reagent system is produced by dissolving 0.010g (0.026 millimole) of pyrocatechol violet, 0.015g (0.0765 millimole) of ammonium molybdate, 0.300g human serum albumin, 0.250g tartaric acid and 0.750g of glycine in a sufficient amount (approximately 70 to 80 mL (milliliter)) of distilled water. The pH of the resulting solution is titrated with an aqueous solution of hydrogen chloride (HCl) to adjust the pH to 2.5. The pH adjusted solution is transferred to a 100 mL volumetric flask, and the total volume is adjusted to 100 mL with distilled water. The final solution includes a 0.26 mM (millimolar) concentration of pyrocatechol violet and 0.76 mM concentration of molybdate. The 0.75g of glycine was added to the specific gravity reagent composition to serve as a buffer and the 0.250g of tartaric acid was added to serve as a chelating agent. In addition, increased amounts of the buffer, glycine, such as up to about 1.875 g per 100 ml of specific gravity reagent composition, or up to about 250 mM (millimolar), can be added to provide a stronger buffering effect.

Furthermore, it also has been found that in addition to the glycine buffer used in the above example, the desired pH can be maintained at an essentially constant level by using any suitable buffer, such as malonate, lactate, succinate, phthalate, citrate, trichloroacetate, sulfosalicylate, tartarate, oxalate, phosphates, acetates, sodium chloride/hydrochloric acid, piperazine-N,N'-bis(2-hydroxypropane)sulfonic acid (POPSO), N-2-hydroxyethyl-piperazine-N'-2ethanesulfonic acid (HEPES), 3-N-(tris-hydroxymethyl) methylamino-2-hydroxypro-panesulfonic acid (TAPSO), 2-([tris-(hydroxymethyl)methyl]-amino)ethanesulfonic acid (TES), or other suitable buffers as are well known in the art. Similarly, in addition to the tartaric acid chelating agent used in the above example, other suitable chelating agents include oxalic acid, malonic acid, succinic acid, citric acid, ethylenediaminetetraacetic acid (EDTA), or other suitable chelating agents as are well known in the art. Furthermore, in some cases the buffer and chelating agent may be the same compound, such as oxalic acid or tartaric acid.

Additionally, the particular molybdate and the particular polyhydroxybenzenesulfonephthalein-type or polyhydroxybenzenephthalein-type dye included in the specific gravity reagent composition do not necessarily have to be present in the approximately 0.33 to 1 molar ratio of dye to molybdate present in the preceding example. As will be discussed more fully hereinafter, by increasing the molar amount of dye, and thereby increasing the dye to molybdate ratio, the protein assay is more sensitive to test sample specific gravities, in that color differentiations between the test sample specific gravities differing by as little as 0.003 are more easily resolved. However, it has been found that a molar ratio of the dye to the molybdate within a range of from about 0.1 to 1 to about 10 to 1, and preferably in the range of from about 0.25 to 1 to about 5 to 1, provides the full advantages and benefits of the present invention.

In addition, it has been found that the amount of protein added to the specific gravity reagent composition should be at least 300 mg protein per 100 ml (300 mg/dL) of the specific gravity reagent composition, or at least 0.3% by weight of the specific gravity reagent composition. Including a protein, such as albumin, in amounts from about 300 mg/dL to about 500 mg/dL in the specific gravity reagent composition ensures that the molybdate-dye complex interacts with and responds to the ionic components of the test sample and not to the albumin that may be present in the test sample.

A specific gravity reagent composition including the molybdate-dye complex as described above can be used in dry phase, test pad assays for specific gravity. The dry phase, test pad assay for specific gravity that utilizes the specific gravity reagent composition is performed in accordance with methods well known in the art. In general, the assay for specific gravity is performed by contacting the urine or other test sample with an analyte detection device that includes the specific gravity reagent composition. The analyte detection device can be dipped into the test sample, or the test sample can be applied to the analyte detection device dropwise. The resulting change in color of the analyte detection device reveals the specific gravity of the test sample; and, if so designed, the resulting color transition can be compared to a standardized color chart to provide a measurement of the specific gravity of the urine or test sample.

Typically, the analyte detection device is a test strip impregnated with a reagent composition, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move, in response to capillary forces, through the matrix to contact the reagent composition and produce a detectable and measurable color transition.

The carrier matrix can be any substance capable of incorporating the chemical reagents required to perform the assay of interest, as long as the carrier matrix is substantially inert with respect to the chemical reagents and does not contaminate the urine or other test samples either by test sample extraction of components comprising the carrier matrix or by appreciably altering the urine or test sample in a way to make the subsequent assays inconclusive, inaccurate or doubtful. The carrier matrix also must be porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like.

Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fibercontaining papers such as filter paper or chromatographic paper; synthetic or modified naturally-occuring polymers, such as cellulose acetate, polyvinyl chloride, polyacrylamide, polyacrylates, polyurethanes, crosslinked dextran, agarose, and other such crosslinked and noncrosslinked waterinsoluble hydrophilic polymers. Hydrophobic and non-absorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix must include a hydrophilic or absorptive material. The handle usually is formed from hydrophobic materials such as cellulose acetate, polyethylene, terephthalate, polycarbonate or polystyrene, and the carrier matrix is most advantageously constructed from bibulous filter paper or nonbibulous permeable polymeric films.

To achieve the full advantage of the present invention, the specific gravity reagent composition including the molybdate-dye complex is impregnated into a suitable carrier matrix and utilized in a dry phase test strip for the specific gravity assay of an aqueous test sample. The method of the present invention affords an economical, accurate and reliable assay for the specific gravity of aqueous test samples that can be performed at home or in the laboratory. In addition, the method of the present invention allows the differentiation and measurement of test sample specific gravities that are very nearly identical, such as specific gravities that differ by only about 0.003, therefore making the specific gravity assay more useful clinically.

In accordance with the method of the present invention, to perform a dry phase, test strip assay for specific gravity, the aqueous solution of the specific gravity reagent composition described above, including from about 0.2 mM to about 2 mM total concentration of a molybdate-dye indicator, such as molybdate-pyrocatechol violet indicator, and including from about 0.2% to about 0.5% of a protein, such as albumin, on a percent weight of protein per volume of specific gravity reagent composition basis (i.e., percent per deciliter), adjusted to and buffered at a pH of 2.5, first is prepared. A bibulous matrix, such as filter paper, like WHATMAN CCP500 filter paper, available commercially from Whatman Ltd., Maidstone, Kent, U.K., then is saturated and impregnated with the aqueous solution of the specific gravity reagent composition containing the molybdate-dye complex indicator and the protein either by spreading, by immersing or by spraying the aqueous solution onto sheets or precut strips of the filter paper. After removing the aqueous solvent by oven drying in an air oven at about 50° C. for about 15 to 20 minutes, the filter paper impregnated with the specific gravity reagent composition is cut to an appropriate size, such as a pad having dimensions from about 0.25 cm by about 0.25 cm to about 1.0 cm by about 1.0 cm. The filter paper impregnated with the specific gravity reagent composition then is secured to an opaque or transparent hydrophobic plastic handle with double sided adhesive tape.

The resulting test strip then was dipped into a fresh, uncentrifuged urine sample for a sufficient time to saturate the test pad with the sample. After waiting a predetermined time, such as from about 1 min. to about 2 min., the test strip is examined, either visually or by instrument, for a response. The degree of color transition of the test pad reveals the specific gravity of the urine sample.

Furthermore, in accordance with another important feature of the present invention, it is well within the experimental techniques of those skilled in the art of preparing test devices to determine the proper balance between size of reagent pad, the strength of specific gravity reagent composition impregnating solution, the identity and amount of molybdate-dye complex, chelating agent, protein and buffer in the specific gravity reagent composition, the amount of test sample, and the method of introducing the test sample to the test strip, such as by pipetting rather than dipping, to provide detectable and differentiable color transitions, such that a comparison, either visually and/or by instrument, to color standards derived from solutions of known specific gravity is possible.

In many cases simple visual observation of the test strip provides the desired information. If more accurate information is required, a color chart bearing color spots corresponding to various standard specific gravities, can be prepared for the particular molybdate-dye complex specific gravity reagent composition used in the test strip. The resulting color of the test strip after contact with the urine sample then can be compared with the color spots on the chart to determine the specific gravity of the test sample.

If a still more accurate determination is required, a spectrophotometer or colorimeter can be used to more precisely determine the degree of the color transition. In addition, the dry phase, reagent strip assay can be made quantitative by employing spectrophotometric or colorimetric techniques, as opposed to visual techniques, in order to more reliably and more accurately measure the degree of color transition, and therefore more accurately measure the specific gravity of the test sample.

As will be discussed more fully hereinafter, the ability of the specific gravity reagent composition to measure and differentiate between specific gravities that differ by as little as 0.003 within the specific gravity range of from about 1.000 and about 1.030 and that differ by as little as 0.005 within the specific gravity range of from about 1.030 to about 1.050 surprisingly and unexpectedly provides an improved method of assaying aqueous test samples for specific gravity. For example, according to present day methods, the accurate measurement of urine specific gravity requires a laboratory technique that is expensive and time-consuming. Accordingly, until the method of the present invention, no dry phase, test strip technique was available to accurately differentiate between and accurately measure urine specific gravities that differ by as little as approximately 0.002. Therefore, in accordance with an important feature of the present invention, it has been demonstrated that by impregnating the specific gravity reagent composition including a molybdate-dye complex into a suitable carrier matrix, the accurate and reliable specific gravity assay of a urine sample can be achieved by using a dry phase test strip.

To show the new and unexpected results arising from using the specific gravity reagent composition of the present invention to differentiate and measure the specific gravity of a test sample, color space plots were made from specific gravity assays using dry phase test strips having a specific gravity reagent composition including a molybdate-dye complex impregnated into a filter paper matrix. The color space plots were obtained by contacting standardized solutions of known specific gravities with the dry phase test strips including the specific gravity reagent composition impregnated into a filter paper carrier matrix.

In general, a color space plot includes three axes, the L*, A* and B* axes. The values of L* plotted on the vertical axis are a measure of the intensity of color, whereby a large L* value denotes a light color and L*=0 denotes a completely black color. The horizontal A* axis is a measure of the color transition from green to red, whereby the more positive the A* value, the more red the color, and analogously, the more negative the A* value, the more green the color. Similarly, the third axis, B*, is a measure of the color transition from blue to yellow, whereby the greater the value of B*, the more yellow the color, and analogously the smaller the value of B*, the more blue the color.

The color space difference ($\Delta E$) is calculated from the following equation (Eq. 1):

$$\Delta E = \sqrt{(L_1^* - L_2^*)^2 + (A_1^* - A_2^*)^2 + (B_1^* - B_2^*)^2} \quad \text{Eq. 1}$$

wherein:

$L_1^*$, $A_1^*$, and $B_1^*$ are the color space values determined for a first standardized solution of known specific gravity;

$L_2^*$, $A_2^*$ and $B_2^*$ are the color space values determined for a second standardized solution of known specific gravity having a different specific gravity from the first standardized specific gravity solution; and $\Delta E$ is the color space difference between the color space plots of the first and second standardized specific gravity solutions.

The color space difference ($\Delta E$) is the straight line distance between two points in a three-dimensional color space plot. Theoretically, a color space difference of 1 unit is the smallest color difference the human eye can distinguish. However, because of the inherent differences between the visual capabilities of individuals, a color space difference ($\Delta E$) of about 5 units is required in order to practically and confidently distinguish between colors.

The L*, A* and B* values plotted on the color space plots are calculated from the percent reflectance measurements taken at sixteen different wavelengths evenly spaced between 400 nm (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values X, Y and Z, and L*, A* and B* are calculated from the X, Y and Z tristimulus values using the following equations:

$$L^* = 116 \times [(Y/Yo)^{\frac{1}{3}} - 16)] \quad \text{(Eq. 2)}$$

$$A^* = 500 \times [(X/Xo)^{\frac{1}{3}} - (Y/Yo)^{\frac{1}{3}}] \quad \text{Eq. 3)}$$

$$B^* = 200 \times [(Y/Yo)^{\frac{1}{3}} - (Z/Zo)^{\frac{1}{3}}] \quad \text{Eq. 4)}$$

wherein:

Xo, Yo and Zo are the tristimulus values for perfect white (i.e. reflectance = 100% at all wavelengths), and X, Y and Z are the tristimulus values calculated as described above from the sixteen wavelengths between 400 nm and 700 nm.

From the color space plots, the color space differences ($\Delta E$) were calculated, and are summarized and discussed in more detail hereinafter. In interpreting the data to be presented, a term such as $\Delta E(1.007-1.012)$ is the color space difference between specific gravity assays for standardized urine solutions having a specific gravity of 1.007 and 1.012. Similarly, the term $\Delta E(1.007-1.020)$ is the color space difference between specific gravity assays for standardized urine solutions having a specific gravity of 1.007 and 1.020. The terms $\Delta E(1.007-1.028)$ and $\Delta E(1.007-1.032)$ are analogously defined. It should be noted that standardized urine solutions having different specific gravities, such as 1.007 and 1.012, also have different ionic strengths because the specific gravity increases when the urine includes more dissolved ionic species, such as cations, like sodium and potassium, and anions, like chloride.

Initially, it was found that the prior art molybdate-dye complex used to assay urine for protein content was severely affected by the specific gravity of the urine sample. TABLE II summarizes a series of assays performed on standardized urine samples containing the same amount of albumin, but having differing ionic strengths and specific gravities due to the addition of sodium chloride.

TABLE II

DEPENDENCE OF PRIOR ART MOLYBDATE-DYE INDICATOR REAGENT SYSTEM UPON IONIC STRENGTH (SPECIFIC GRAVITY)

| Specific Gravity of Urine Containing No Albumin | Color Transition of Molybdate-Dye Indicator Reagent |
| --- | --- |
| 1.007 | Blue |
| 1.012 | Lt. Blue, and some gray |
| 1.020 | Gray, and some brown & yellow |
| 1.028 | Gray, and some brown & yellow |
| 1.032 | Gray, and some brown & yellow |

In Table II, the molybdate-dye indicator reagent was prepared by adding 75 mg of human albumin to a 25 ml volumetric flask, then filling the flask to a volume of 25 ml. with an ammonium molybdatepyrocatechol violet-tartaric acid indicator solution, adjusted to and buffered at a pH of 2.5. This solution contains the equivalent of 300 mg/dL of albumin. The molybdate-dye reagent was impregnated into WHATMAN CCP500 filter paper and cut into strips, as described above. The test strips then were dipped into a urine samples, each containing no albumin and each having different specific gravity and ionic strength due to the addition of sodium chloride. It is readily observed in TABLE II that the molybdate-dye indicator reagent changed color from blue to grayish brown upon an ionic strength increase and a specific gravity increase from 1.007 to 1.020 even though the albumin content in the test sample remained unchanged. In addition, a molybdatedye indicator reagent containing 400 mg/dL gave identical results, both in assays of urine samples containing no albumin and in assays of urine samples containing 15 mg/dL of albumin. These results demonstrate that the molybdate-dye complex reagent changes color in response to urine specific gravity and ionic strength.

In addition, if the urine sample specific gravity is increased, but the ionic strength held constant, such as by adding glucose rather than sodium chloride to the urine sample, the color transitions observed in TABLE II due to an increase in specific gravity do not occur, showing that the molybdate-dye indicator reagent is more sensitive to the ionic strength changes of the urine sample than to the absolute specific gravity changes of the urine. As demonstrated above, and as will be discussed more fully hereinafter, it was found that accurate urine specific gravity assays are achieved by using test strips incorporating the specific gravity reagent composition of the present invention because of the dependence of the color transition of the molybdate-dye complex on test sample ionic strength.

The results summarized in TABLE II for the molybdate-dye indicator reagent are quantified in TABLE III, wherein color space plots were obtained for assays of urine samples having different albumin concentrations and different specific gravities and ionic strengths to demonstrate the large effect of urine specific gravity on the color transition of the molybdate-dye indicator reagent. It was found that varying the specific gravity of the urine sample by adding glucose did not have a pronounced effect on the assays using the molybdate-dye complex specific gravity method because $\Delta E$ (1.007–1.015) is 2.24 units and $\Delta E$ (1.007–1.022) is 1.21 units, both below the minimum visually detectable level of about 5 units. However, TABLE III shows that using sodium chloride to increase the specific gravity of the urine sample containing no albumin also increases the ionic strength of the urine sample, and therefore, an accurate specific gravity assay using the method of the present invention results. A careful examination of TABLE III shows that the color space differences obtained for test samples having an albumin content of essentially zero but differing ionic strengths and specific gravities exceeds 5 units, therefore showing that a visible color difference will be detected by the human assayer. In addition, it has been found that even if the urine sample has an increased amount of albumin, the color space difference due to specific gravity remains relatively constant. Therefore, the amount of albumin present in the urine sample affects the specific gravity assay only minimally, and as will be discussed further hereinafter, the intentional addition of relatively large amounts of albumin to the specific gravity reagent composition effectively eliminates this minor interference.

TABLE III $\Delta E$ DIFFERENCES IN ASSAYS USING THE MOLYBDATE-DYE COMPLEX SPECIFIC GRAVITY REAGENT BETWEEN TEST SAMPLES HAVING DIFFERENT SPECIFIC GRAVITIES/IONIC STRENGTHS AND CONTAINING ESSENTIALLY NO ALBUMIN

| | $\Delta E$ | $\Delta E$ | $\Delta E$ | $\Delta E$ |
|---|---|---|---|---|
| Albumin Conc. | (1.007– 1.0012) | (1.012– 1.021) | (1.021– 1.026) | (1.026– 1.032) |
| 0 mg/dL | 13.76 | 9.81 | 7.79 | 5.37 |

In accordance with the method and composition of the present invention, from TABLE III, using the molybdate-dye complex in a specific gravity reagent composition, all of the color space differences are well above the minimum human detectable limit of approximately 5 units, therefore providing a specific gravity assay of the test sample. The color space difference values are above approximately 5, therefore a color change is discernible by the human eye, and the assayer can differentiate between urine samples having specific gravities differing by as little as 0.003 in the specific gravity range of about 1.000 to about 1.030 and by as little as 0.005 in the specific gravity range of about 1.030 to about 1.050.

TABLE IV

COLOR SPACE DIFFERENCES FOR ASSAYS USING THE MOLYBDATE-DYE COMPLEX INDICATOR REAGENT COMPOSITION CONTAINING 300 mg/dL OF ALBUMIN IN RESPONSE TO TEST SAMPLES CONTAINING DIFFERENT ALBUMIN CONTENT AND IONIC STRENGTHS

| Specific Gravity (adjusted with Sodium Chloride) | $\Delta E$ (Alb 15-0) | $\Delta E$ (Alb 30-0) | $\Delta E$ (Alb 100-0) |
|---|---|---|---|
| 1.007 | 1.11 | 1.10 | 3.10 |
| 1.012 | 2.26 | 2.20 | 2.49 |
| 1.020 | 0.52 | 1.18 | 0.99 |
| 1.028 | 1.94 | 0.66 | 1.95 |
| 1.032 | 1.32 | 1.91 | 1.51 |

TABLE IV, wherein the molybdate-dye indicator reagent used in the assays of TABLE II is used as the indicator to assay for the specific gravity of a test sample, shows color space differences of substantially less than 5 units as the albumin content of the test sample varies. As a result, a urine sample albumin content of up to about 100 mg/dL would not appreciably interfere with a specific gravity assay of the present invention because regardless of the urine albumin content, the $\Delta E$ values range only from 0.99 units to 3.10 units, or below the minimum visually detectable levels. For example, a specific gravity assay of a test sample containing either 30 mg/dL or 15 mg/dL of albumin would not be erroneous due to the protein content of the test sample because the color space difference between the test samples containing 15 mg/dL and 30 mg/dL ranges only from about 0.5 units to about 2.3 units, well below the minimum visually detectable change of at approximately 5 units for humans.

TABLE V is identical to TABLE IV except that the indicator reagent composition includes 400 mg/dL of albumin. The results tabulated in TABLE V again show color space differences significantly less than the minimum visually detectable level of 5 units. Therefore, TABLES IV and V show that upon incorporating a sufficient amount of a protein, like albumin, into the specific gravity reagent composition that is introduced into a carrier matrix of a test strip, the color transition of the specific gravity reagent composition occurs in response to the specific gravity/ionic strength of the test sample, and is not affected by the albumin content of the test sample. For test sample albumin in concentrations of up to at least about 100 mg/dL the color space differences range from about 0.5 to about 2.5, and therefore are beyond the ability of the normal human eye to discriminate.

TABLE IV

COLOR SPACE DIFFERENCES FOR ASSAYS USING THE MOLYBDATE-DYE COMPLEX INDICATOR REAGENT COMPOSITION CONTAINING 400 mg/dL OF ALBUMIN IN RESPONSE TO TEST SAMPLES CONTAINING DIFFERENT ALBUMIN CONTENT AND IONIC STRENGTHS

| Specific Gravity (adjusted with Sodium Chloride) | ΔE (Alb 15-0) | ΔE (Alb 30-0) | ΔE (Alb 100-0) |
|---|---|---|---|
| 1.007 | 1.11 | 1.40 | 1.88 |
| 1.012 | 0.94 | 1.81 | 2.13 |
| 1.020 | 0.48 | 2.40 | 1.22 |
| 1.028 | 0.94 | 1.87 | 1.04 |
| 1.032 | 0.56 | 0.84 | 0.49 |

As a result, it has been demonstrated, that using the molybdate-dye complex in a specific gravity reagent composition as an indicator to differentiate and measure the specific gravity of a test sample, surprisingly and unexpectedly allows the accurate and reliable specific gravity determination of test samples having approximately the same specific gravity, without the specific gravity assay being adversely influenced by the nonionic components, such as albumin and/or glucose, of the test sample. Such unexpected improvements provide an important and useful benefit over the prior art indicators used to assay for the specific gravity of test samples. As illustrated in the previous tables, the molybdate-dye complex included in the specific gravity reagent composition responds to the ionic strength of the test sample, is relatively unaffected by the nonionic components of the test sample, and therefore provides an accurate specific gravity assay.

It should be understood that those skilled in the art of designing test kits are able to design an optimal test strip incorporating a sufficient amount and a particularly effective molybdate-dye indicator specific gravity reagent composition to permit the differentiation and measurement of test sample specific gravities differing by as little as 0.003, as present tests utilizing the method and composition of the present invention show a color space difference of at least approximately 5 units. This ΔE value is usually sufficient for detection by the human eye, and can be easily detected by present day colorimeters and/or spectrophotometers. Similarly, the method and composition of the present invention provide an accurate specific gravity assay regardless of varying amounts of test sample nonionic components, such as glucose or albumin, in amounts normally found in human fluids, as long as sufficient ionic components are present in the test sample to cause a color transition that can be correlated to test sample specific gravity.

In accordance with another important feature of the present invention, it has been found that full color development of test strips containing the molybdate-dye complex as the indicator in a specific gravity reagent composition occurs within about 1 min. to about 3 min. after contacting the test strip with the test sample. Maximum color development occurs after about 2 min. of contact. However, acceptable and trustworthy specific gravity assay results are achieved when the test strip is examined for a color change about one minute after contact with the test sample. Such a short time for full color development of the test strip is an additional advantage of the specific gravity reagent composition of the present invention over the molybdate-dye complex of the prior art composition used to assay for proteins that required approximately 10 minutes for maximum color development. Therefore, test strips incorporating the molybdate-dye specific gravity reagent composition of the present invention can be used to obtain faster and more accurate specific gravity assays. It should be noted that for all of the specific gravity assays summarized in the tables, the test strips incorporating the molybdate-dye complex reagent composition were examined for a response after a 2 minute contact time. It also has been found that the color transition resulting from a test sample and molybdate-dye complex interaction is stable over time.

It has been demonstrated that the change in color space difference between about one minute and about 2 minutes is relatively small, such that accurate assays will result about one minute after contact between the urine and the test strip incorporating the molybdate-dye specific gravity reagent composition. Furthermore, it is seen that a urine sample containing varying amounts of albumin, or other nonionic components, may be accurately assayed by visual detection and measurement methods, because these nonionic urine components do not sufficiently interfere with the assay to generate a color space difference above the minimum required for differentiation by the human eye. Furthermore it has been found that a molar ratio of molybdate to dye of from about 3 to about 1 to about 1 to about 5 provides an indicator suitable for a specific gravity reagent composition to provide heightened sensitivity to the specific gravity of an aqueous test sample.

Overall, it has been shown that a molybdate-dye complex included in a specific gravity reagent composition impregnated into a suitable carrier matrix, such as filter paper, improves color differentiation between test samples having specific gravities differing by as little as 0.003 for test samples having a specific gravity of from about 1.000 to about 1.030 and by as little as 0.005 for test samples having a specific gravity of from about 1.030 to about 1.050, and therefore improves the sensitivity of the specific gravity assays of aqueous test samples. In addition to increased sensitivity over the prior art specific gravity assay methods, the method and composition of the present invention is not subject to detectable interferences from various nonionic test sample components, and provides full color development and accurate assay results in a relatively short time. The method and composition of the present invention also allows visual differentiation of color transitions resulting from contact of the carrier matrix impregnated with the molybdate-dye complex specific gravity reagent composition between test samples having specific gravities differing by as low as 0.002, thereby providing accurate and trustworthy specific gravity assays of test samples.

Therefore, in accordance with an important feature of the present invention, more accurate and reliable assays for the specific gravity of urine and other liquid test samples can be performed by utilizing a molybdate-dye complex, a chelating agent and a sufficient amount of a protein in a specific gravity reagent composition. The molybdate-dye indicator improves the color differentiation between test samples having nearly equal specific gravities and therefore improves assay sensitivity. The intentionally added protein overcomes and negates any interferences arising due to the protein content of the test sample.

Obviously, many modifications and variations of the invention as hereinbefore set forth can be made without departing from the spirit and scope thereof and therefore only such limitations should be imposed as are indicated by the appended claims.

We claim:

1. A composition capable of exhibiting within three minutes sufficient color transition in response to ionic strength to differentiate by ±0.003 between aqueous test samples having specific gravities ranging from about 1.000 to about 1.030 and by ±0.005 between aqueous test samples having specific gravities ranging from about 1.030 to about 1.050, said composition consisting essentially of:

a water-soluble molybdate; a polyhydroxybenzenesulfonephthalein dye and/or a polyhydroxybenzenephthalein dye; a chelating agent; a sufficient amount of a protein to eliminate the color interference effects of protein present in the aqueous test sample; and a buffer to maintain the composition at an acidic pH.

2. The composition of claim 1 wherein the polyhydroxybenzenesulfonephthalein dye or polyhydroxybenzenephthalein dye is selected from the group consisting of pyrocatechol violet, pyrogallol red, bromopyrogallol red, xylenol orange, pyrogallol phthalein and o-hydroxyhydroquinonphthalein; or combinations thereof.

3. The composition of claim 1 wherein the chelating agent is selected from the group consisting of the free acid or the water-soluble salts of tartaric acid, oxalic acid, malonic acid, succinic acid, citric acid, ethylenediaminetetraacetic acid (EDTA), gluconic acid, N-(hydroxyethyl)ethylenediaminetriacetic acid (HEEDTA), nitrilotriacetic acid (NTA), diethylenetriaminepentaacetic acid (DTPA), aminotris(methylene phosphonic acid), hydroxy-ethylidene diphosphonic acid, hexamethylenediaminetetra(methylene phosphonate), ethylenediaminediacetic acid (EDDA), iminodiacetic acid (IDA), nitrilopropionic acid (NTP), hydroxyethyliminodiacetic acid (HIDA), pyrophosphoric acid, 1-hydroxyethane-1,1-diphosphonic acid, tripolyphosphoric acid, hexametaphosphoric acid and metaphosphoric acid; or combinations thereof.

4. The composition of claim 1 wherein the protein is albumin.

5. The composition of claim 1 wherein the buffer is selected from the group consisting of lactate, glycine, phthalate, trichloroacetate, sulfosalicylate, phosphates, acetates, piperazine-N,N'-bis(2-hydroxypropane)sulfonic acid (POPSO), N-2- hydroxyethyl-piperazine-N'-2-ethanesulfonic acid (HEPES), 3-N-(tris-hydroxymethyl)methylamino-2-hydroxypro-panesulfonic acid (TAPSO) and 2-([tris(hydroxymethyl)methyl]-amino)ethanesulfonic acid (TES); or combinations thereof.

6. The composition of claim 1 wherein the buffer is present in a concentration of from about 100 mM to about 500 mM.

7. The composition of claim 1 wherein the water-soluble molybdate is a molybdate selected from the group consisting of ammonium molybdate, sodium molybdate, bismuth molybdate, cadmium molybdate, calcium molybdate, lithium molybdate, magnesium molybdate, potassium molybdate, strontium molybdate, zinc molybdate, alkylammonium or hydroxyalkylammonium molybdates, dialkylammonium or di(hydroxyalkyl)ammonium molybdates, trialkylammonium or tri(hydroxyalkyl)ammonium molybdates and ammonium phosphomolybdates; or combinations thereof.

8. The composition of claim 7 wherein the water-soluble molybdate is selected from the group consisting of ammonium molybdate, potassium molybdate, sodium molybdate, lithium molybdate, strontium molybdate, ammonium phosphomolybdate, alkylammonium or hydroxyalkylammonium molybdates, dialkylammonium or di(hydroxyalkyl)ammonium molybdate and trialkylammonium or tri(hydroxyalkyl)ammonium molybdates; or combinations thereof.

9. The composition of claim 1 wherein the chelating agent is present in an amount of at least 0.1% by weight of the composition.

10. The composition of claim 9 wherein the chelating agent is present in an amount of from 0.1% by weight of the composition to about 2% by weight of the composition.

11. The composition of claim 1 wherein the protein is present in an amount of at least 0.3% by weight of the composition.

12. The composition of claim 11 wherein the protein is present in an amount of from 0.3% by weight of the composition to about 0.5% by weight of the composition.

13. The composition of claim 1 buffered in a pH range of approximately 2 to approximately 4.

14. The composition of claim 13 buffered in a pH range of approximately 2.5 to approximately 3.5.

15. The composition of claim 1 wherein the molar ratio of the polyhydroxybenzenesulfonephthalein dye and/or polyhydroxybenzenephthalein dye to the water-soluble molybdate is within a range of from about 0.1 to 1 to about 10 to 1.

16. The composition of claim 15 wherein the molar ratio of the polyhydroxybenzenesulfonephthalein dye and/or polyhydroxybenzenephthalein dye to the water-soluble molybdate is within a range of from about 0.25 to 1 to about 5 to 1.

17. A composition for measuring the specific gravity of urine comprising a water-soluble molybdate; a polyhydroxybenzenesulfonephthalein dye and/or a polyhydroxybenzenephthalein dye; a chelating agent; a sufficient amount of a protein to eliminate the color interference effects of any protein present in the urine; and a buffer to maintain the composition at an acidic pH.

18. The composition of claim 17 wherein the polyhydroxybenzenesulfonephthalein dye or polyhydroxybenzenephthalein dye is selected from the group consisting of pyrocatechol violet, pyrogallol red, bromopyrogallol red, xylenol orange, pyrogallol phthalein and o-hydroxyhydroquinonphthalein; or combinations thereof.

19. The composition of claim 17 wherein the chelating agent is selected from the group consisting of the free acid or the water-soluble salts of tartaric acid, oxalic acid, malonic acid, succinic acid, citric acid, ethylenediaminetetraacetic acid (EDTA), gluconic acid, N-(hydroxyethyl)ethylenediaminetriacetic acid (HEEDTA), nitrilotriacetic acid (NTA), diethylenetriaminepentaacetic acid (DTPA), aminotris(methylene phosphonic acid), hydroxy-ethylidene diphosphonic acid, hexamethylenediaminetetra(methylene phosphonate), ethylenediaminediacetic acid (EDDA), iminodiacetic acid (IDA), nitrilopropionic acid (NTP), hydroxyethyliminodiacetic acid (HIDA), pyrophosphoric acid, 1-hydroxyethane-1,1-diphosphonic acid, tripolyphosphoric acid, hexametaphosphoric acid and metaphosphoric acid; or combinations thereof.

20. The composition of claim 17 wherein the protein is albumin.

21. The composition of claim 17 wherein the buffer is selected from the group consisting of lactate, glycine, phthalate, trichloroacetate, sulfosalicylate, phosphates, acetates, piperazine-N,N'-bis(2-hydroxypropane)sulfonic acid (POPSO), N-2-hydroxyethyl-piperazine-N'-2-ethanesulfonic acid (HEPES), 3-N(tris-hydroxymethyl)methylamino-2-hydroxypro-panesulfonic acid (TAPSO) and 2-[tris(hydroxymethyl)methyl]-amino)ethanesulfonic acid (TES); or combinations thereof.

22. The composition of claim 17 wherein the buffer is present in a concentration of from about 100 mM to about 500 mM.

23. The composition of claim 17 wherein the water-soluble molybdate is a molybdate selected from the group consisting of ammonium molybdate, sodium molybdate, bismuth molybdate, cadmium molybdate, calcium molybdate, lithium molybdate, magnesium molybdate, potassium molybdate, strontium molybdate, zinc molybdate, alkylammonium or hydroxyalkylammonium molybdates, dialkylammonium or di(hydroxyalkyl)ammonium molybdates, trialkylammonium or tri(hydroxyalkyl)ammonium molybdates and ammonium phosphomolybdates; or combinations thereof.

24. The composition of claim 23 wherein the water-soluble molybdate is selected from the group consisting of ammonium molybdate, potassium molybdate, sodium molybdate, lithium molybdate, strontium molybdate, ammonium phosphomolybdate, alkylammonium or hydroxyalkylammonium molybdates, dialkylammonium or di(hydroxyalkyl)ammonium molybdate and trialkylammonium or tri(hydroxyalkyl)-ammonium molybdates; or combinations thereof.

25. The composition of claim 17 wherein the chelating agent is present in an amount of at least 0.1% by weight of the composition.

26. The composition of claim 25 wherein the chelating agent is present in an amount of from 0.1% by weight of the composition to about by weight of the composition.

27. The composition of claim 17 wherein the intentionally added protein is present in an amount of at least 0.3% by weight of the composition.

28. The composition of claim 27 wherein the intentionally added protein is present in an amount of from 0.3% by weight of the composition to about 0.5% by weight of the composition.

29. The composition of claim 17 buffered in a pH range of approximately 2 to approximately 4.

30. The composition of claim 29 buffered in a pH range of approximately 2.5 to approximately 3.5.

31. The composition of claim 17 wherein the molar ratio of the polyhydroxybenzenesulfonephthalein dye and/or polyhydroxybenzenephthalein dye to the water-soluble molybdate is within a range of from about 0.1 to 1 to about 10 to 1.

32. The composition of claim 31 wherein the molar ratio of the polyhydroxybenzenesulfonephthalein dye and/or polyhydroxybenzenephthalein dye to the water-soluble molybdate is within a range of from about 0.25 to 1 to about 5 to 1.

* * * * *